United States Patent [19]

Katz et al.

[11] Patent Number: 4,504,667

[45] Date of Patent: Mar. 12, 1985

[54] PROCESS FOR OXIDIZING HALOPYRIDINES TO HALOPYRIDINE-N-OXIDES

[75] Inventors: Lawrence E. Katz, Orange; Richard H. Dumas, East Haven, both of Conn.

[73] Assignee: Olin Corporation, Cheshire, Conn.

[21] Appl. No.: 507,410

[22] Filed: Jun. 24, 1983

[51] Int. Cl.³ .......................................... C07D 213/61
[52] U.S. Cl. ................................................... 546/345
[58] Field of Search ........................ 546/345; 549/526

[56] References Cited

U.S. PATENT DOCUMENTS

| | | | |
|---|---|---|---|
| 2,686,786 | 8/1954 | Shaw et al. | 260/294.8 |
| 2,951,844 | 9/1960 | Shermer | 260/290 |
| 3,047,579 | 7/1962 | Witman | 260/289 |
| 3,203,957 | 8/1965 | Kirchner | 260/290 |
| 3,892,760 | 7/1975 | Pitts | 260/294.8 J |
| 3,954,781 | 5/1976 | Pitts | 260/294.8 |
| 4,080,329 | 3/1978 | Muntwyler | 260/294.8 G |

FOREIGN PATENT DOCUMENTS

| | | | |
|---|---|---|---|
| 0036638 | 9/1981 | European Pat. Off. | 546/345 |
| 847701 | 9/1960 | United Kingdom | 546/345 |

OTHER PUBLICATIONS

G. C. Finger and L. D. Starr, "Aromatic Fluorine Compounds IX. 2-Fluoro-pyridines", J. Am. Chem. Soc., vol. 81, pp. 2674-2675, (Jun. 5, 1959).

R. F. Evans and J. C. Brown, J. Organic Chemistry, vol. 27, pp. 1329 et seq., (1962).

Katritzky, J. Chem. Soc., vol. 1957, pp. 191 et seq.

D. Sarantakis, J. K. Sutherland, C. Tortorella & V. Tortorella; "2 Fluoropyridine-N-Oxide in Peptide Chem.", Chem. Comm., No. 4, pp. 105-106, (1966).

R. J. Kennedy and A. M. Stock, "The Oxidation of Organic Substances by Potassium Peroxymonosulfate", J. or Organic Chem., vol. 25, 1901, (1960).

Literature Search 80-136; Olin Corporation, Jul. 21, 1980.

Correspondence relating to work done by Olin Corporation, FMC and DuPont in the early 1960's.

*Primary Examiner*—Henry R. Jiles
*Assistant Examiner*—Robert C. Whittenbaugh
*Attorney, Agent, or Firm*—William A. Simons; Thomas P. O'Day

[57] ABSTRACT

Described is a process for oxidizing 2-chloropyridine or 2-bromopyridine to the corresponding N-oxide with peracetic acid generated in-situ from $H_2O_2$ and acetic acid in the presence of a catalyst selected from the group consisting of maleic acid, maleic anhydride, phthalic anhydride, and mixtures thereof.

11 Claims, No Drawings

4,504,667

PROCESS FOR OXIDIZING HALOPYRIDINES TO HALOPYRIDINE-N-OXIDES

BACKGROUND OF THE INVENTION

1. Field of the Invention

The present invention relates to a process for making selected halopyridine-N-oxides by the oxidation of the corresponding halopyridine with peracetic acid generated in-situ. In particular, the present invention relates to a process for making 2-chloropyridine-N-oxide or 2-bromopyridine-N-oxide by the oxidation of the corresponding halopyridine with peracetic acid generated in-situ from acetic acid and $H_2O_2$ while in the presence of a catalyst selected from the group consisting of maleic acid, maleic anhydride, phthalic anhydride, and mixtures thereof.

2. Description of the Prior Art

2-Chloropyridine and 2-bromopyridine are chemical intermediates which may be converted to the sodium and zinc salts of pyridine-2-thiol-N-oxide. See U.S. Pat. Nos. 2,686,786 and 3,203,957, which issued to Shaw et al. on Aug. 17, 1954, and Kirchner on Aug. 31, 1965, respectively. These compounds may also be converted to bis (2-pyridyl-1-oxide) disulfide. See U.S. Pat. Nos. 3,892,760 and 3,954,781, both of which issued to Hooks, Jr. and Pitts on July 1, 1975, and May 4, 1976, respectively. All of these end products are excellent biocides and have been used in hair shampoos or skin cleansing preparations, or the like.

Because 2-chloropyridine-N-oxide is generally more economic to make, most of the work centered around improving its preparation. However, the procedures disclosed herein for making 2-chloropyridine-N-oxide may be practiced to convert 2-bromopyridine to its N-oxide with generally similar results.

In the past, 2-chloropyridine-N-oxide had been made from 2-chloropyridine by various methods. As shown in U.S. Pat. No. 2,951,844 which issued to Shermer on Sept. 6, 1960, 2-chloropyridine may be reacted with an aqueous peracetic acid solution in a mole ratio of 0.4 to 0.8 mole of peracetic acid per mole of 2-chloropyridine. The peracetic acid content of the aqueous solution may be preferably about 30 to 50 weight percent. This reaction may be shown by the following equation (A):

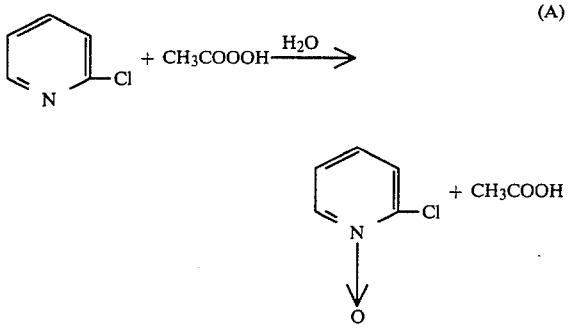

(A)

Upon reaction completion, the reaction mixture may be then neutralized with a base to a pH of 5 to 8, converting the acetic acid by-product to an acetate salt, for example, by using an aqueous NaOH solution. The unreacted 2-chloropyridine is recovered from the reaction mixture by distillation. Shermer teaches that a convenient method for preparing the peracetic acid comprises mixing 70 parts by weight of glacial acetic acid with 30 parts by weight of $H_2O_2$ in the presence of one part of sulfuric acid. The resulting mixture contains about 40% peracetic acid, 40% acetic acid, 15% water, and 5% $H_2O_2$ (with less than 1% $H_2SO_4$). See col. 2, lines 5–11 of this patent.

This "Preformed Peracetic Acid Oxidation Route" as taught by Shermer has several disadvantages. Peracetic acid is relatively unstable which makes its storage a problem. Also, there are a limited number of suppliers which may make it relatively expensive. Further, since excess 2-chloropyridine is used as a starting material, low batch productivity results and greater reactor volumes are needed. Still further, because more total acid is used, more base is needed for neutralization and the effluent from the process will have a high biological oxygen demand (BOD).

Finger and Starr in "Aromatic Fluorine Compounds. IX. 2-Fluoropyridines", J. Am. Chem. Soc., Vol. 81, pages 2674 and 2675 (1959) teach another "Preformed Peracetic Acid Oxidation Route". They reacted 2-chloropyridine with a commercial 40% by weight peracetic acid solution in the presence of extra acetic acid. The mole ratio of 2-chloropyridine to total acid was 1:6.9. This high molar ratio has the same disadvantages of Shermer, but, more so.

In U.S. Pat. No. 3,203,957, which issued to Kirchner on Aug. 31, 1965, 2-chloropyridine-N-oxide is made by oxidizing 2-chloropyridine with $H_2O_2$ and maleic or phthalic anhydride at a temperature in the range from 30° C. to about 90° C., The mole ratio of $H_2O_2$ to 2-chloropyridine may be from 0.5:1 to 1.2:1 and the mole ratio of maleic or phthalic anhydride to $H_2O_2$ is at least 1:1. The reaction may be preferably carried out in the presence of an inert solvent simply for the purpose of facilitating physical handling of the reaction mixture. Kirchner also teaches that the reaction involves the in-situ formation of monoperoxymaleic or monoperoxyphthalic acid.

This "Monoperoxy-Maleic or Phthalic Anhydride Oxidation Route" also has several disadvantages. First, the use of the maleic and phthalic anhydride as reactants are relatively more expensive than acetic acid. Also, the presence of the by-product sodium maleate or sodium phthalate after neutralization sometimes presents problems in making later end products.

For practical purposes, the process taught by Kirchner requires an inert solvent or excess 2-chloropyridine. The use of an inert solvent or excess 2-chloropyridine contributes to lower batch productivity and the use of the former also may require a separation step.

Besides the above-noted patented methods for making 2-chloropyridine-N-oxide, other processes have been described in the literature. R. F. Evans and H. C. Brown [J. Org. Chem., 27, 1329 (1962)] taught that 2-chloropyridine-N-oxide may be prepared by reacting 2-chloropyridine with glacial acetic acid and $H_2O_2$ at 70°–80° C. for about 12 hours without the use of any catalyst. However, they employed an acetic acid to 2-chloropyridine mole ratio of about 10.5:1. Katritzky [J. Chem. Soc., 191 (1957)] also describes the making of 2-chloropyridine-N-oxide by reacting 2-chloropyridine with acetic acid and aqueous $H_2O_2$ without any catalyst overnight at 80° C. Again, he employed an acetic acid to 2-chloropyridine mole ratio of about 13.2:1. The use of these exorbitant molar quantities of acetic acid and long reaction times does result in low batch productivity; require large amounts of NaOH for neutralization;

and result in a high BOD in the waste water effluent from the process. This non-catalytic in-situ technique is only of academic interest and has limited practical application.

Work was also carried out wherein 2-chloropyridine was oxidized with peracetic acid formed in-situ by the reaction of acetic acid and $H_2O_2$ in the presence of an acid cation exchange resin catalyst (i.e., a sulfonated copolymer of styrene and 8% divinyl-benzene). See Example VI of U.S. Pat. No. 3,203,957, which issued to Kirchner. The patent admits this technique for oxidizing 2-chloropyridine to 2-chloropyridine-N-oxide was inferior. It should be noted that this reaction resulted in the low consumption of $H_2O_2$ (74.6%). This means the reaction rate will be relatively slow and methods for disposing of the unreacted $H_2O_2$ must be employed.

Non-published work has been carried out at Olin Corporation for making 2-chloropyridine-N-oxide by reacting 2-chloropyridine with acetic acid and $H_2O_2$ in the presence of very small amounts of $H_2SO_4$ (0.02 mole of $H_2SO_4$ per 1.0 mole of 2-chloropyridine reactant). Furthermore, this work employed an excess of 2-chloropyridine over $H_2O_2$ (1.0 mole:0.6 mole). The excess 2-chloropyridine contributed to low batch productivity.

In U.S. Pat. No. 3,047,579, which issued to Witman on July 31, 1962, 2-chloropyridine may be oxidized with $H_2O_2$ to 2-chloropyridine-N-oxide in the presence of unstable inorganic per-compounds of the acid-forming elements of groups VA, VIA VIB, and VIII" of the periodic table (e.g. pertungstic acid) as catalysts. Witman also teaches that this type of catalyzed reaction may be most effectively carried out in a liquid phase reaction medium, using a lower aliphatic monocarboxylic acid such as glacial acetic acid. Se Col. 5, line 44 to Col. 6, line 5 of this patent.

This "Tungsten Catalyzed Oxidation Route" also has some disadvantages. While higher batch productivity maybe more consistently achieved than in the above-discussed preformed peracetic acid route, the expensive tungsten catalyst must be recovered from the reaction mixture for economic reasons. However, there may be some carry-over of the tungsten with the 2-chloropyridine-N-oxide product. This carry-over which is extremely difficult to prevent, may result in undesirably colored sodium or zinc salts of pyridine-2-thiol-N-oxide later made from this product.

In all, the conversion and selectivity of 2-chloropyridine to 2-chloropyridine-N-oxide with some of these prior art processes have not been appreciably high, especially in large-scale production modes. Therefore, there is a need to raise the conversion and selectivity of this reaction and similar reactions to lower the costs of producing the N-oxide products and products derived from them. Furthermore, the production of zinc pyridine-2-thiol-N-oxide from 2-chloropyridine-N-oxide produced by these prior art processes has sometimes been associated with serious color problems (i.e., this zinc salt has been too dark) which prevent it from being used in certain shampoo formulations. As stated above, it is believed that these color problems are caused by the presence of by-products of the desired N-oxide product. Thus, there is also a need to produce N-oxide products which do not have an appreciable amount of by-products which effect undesirable colors to final products. Furthermore, as can be seen from the discussion above, higher batch productivity and reduced organic effluents are desired.

U.S. patent application Ser. No. 362,707, filed by M. Boudakian on Mar. 26, 1982, presented a solution to those needs. This application teaches a process for oxidizing 2-chloropyridine or 2-bromopyridine to the corresponding N-oxide with peracetic acid in the presence of a catalyst selected from the group consisting of sulfuric acid, alkali metal bisulfates, ammonium bisulfate, and mixtures thereof. While this process results in a higher selectivity and yields than prior art processes and the color of the resultant zinc pyridine-2-thiol-N-oxide made from the 2-chloropyridine-N-oxide product is generally acceptable, there is a need in some instance generally to produce an even whiter and purer product. By the present invention, very white products may be made without sacrificing selectivity and yields.

BRIEF SUMMARY OF THE INVENTION

Accordingly, the present invention is directed to a process for oxidizing 2-chloropyridine or 2-bromopyridine to the corresponding N-oxide with peracetic acid generated in-situ from $H_2O_2$ and acetic acid comprising reacting at a temperature from about 20° C. to about 120° C. (a) hydrogen peroxide, (b) a 2-halo-pyridine selected from the group consisting of 2-chloropyridine and 2-bromopyridine, and (c) acetic acid in the presence of a catalyst selected from the group consisting of maleic acid, maleic anhydride and phthalic anhydride, and mixtures thereof, in order to make the corresponding 2-halopyridine-N-oxide; this reaction carried out by employing from about 0.5 to about 5.0 moles of $H_2O_2$ per mole of 2-halopyridine; employing from about 0.5 to about 2.0 moles of acetic acid per mole of 2-halopyridine and employing from about 0.1 to about 0.8 mole of catalyst per mole of 2-halopyridine.

DETAILED DESCRIPTION

The present invention is an improvement over the above-discussed methods for making 2-halopyridines. Specifically, this invention is characterized by the use of peracetic acid as an oxidizing agent for converting a 2-halopyridine to a 2-halopyridine-N-oxide. The peracetic acid is generated in-situ (i.e., formed and used in the presence of the 2-halopyridine) from $H_2O_2$ and acetic acid in the presence of certain amounts of selected catalysts. The process of this invention may be illustrated by the following equation (B) wherein 2-chloropyridine is utilized.

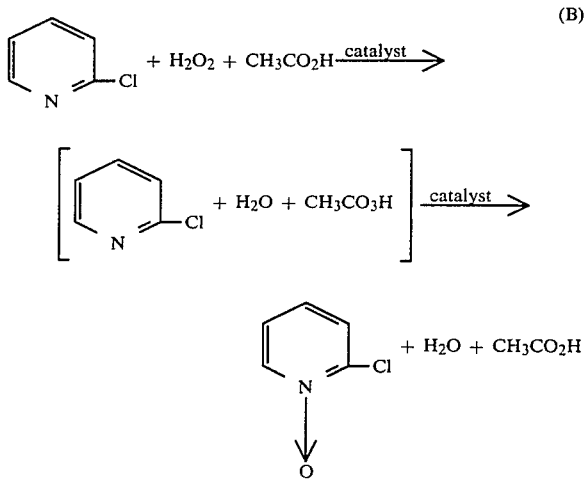

The 2-halopyridine reactants of the present invention may be either 2-chloropyridine or 2-bromopyridine. Both of these compounds are well known and they may be made by many conventional methods. Because of cost considerations, 2-chloropyridine is favored over 2-bromopyridine as a chemical intermediate.

The acetic acid reactant is also a well known and widely available commercial product. For purposes of this invention, 100% by weight glacial acetic acid solutions are preferred. Aqueous solutions (down to 50% by weight acetic acid) of acetic acid may be employed. The use of $H_2O$ in the reaction mixture is not critical. The use of some water may be beneficial since it could work as a heat transfer agent and increase the rate of reaction. Of course, the use of too much water will increase the reaction volume and thus decrease the batch efficiency.

The third reactant, $H_2O_2$, of the present invention is also a widely available commercial product. It is generally available in aqueous solutions containing from about 30% to about 90% by weight of $H_2O_2$. Because there are severe handling problems (e.g., possibility of explosions) at the very high concentrations and low productivity at the very low concentrations, it is preferred to employ $H_2O_2$ in aqueous solutions containing about 40% to about 70% by weight $H_2O_2$.

A critical feature of the present invention is carrying out the in-situ generation of peracetic acid and the reaction to the corresponding N-oxide in the presence of certain amounts of selected catalysts. These catalysts may be maleic acid, maleic anhydride, phthalic anhydride, or mixtures thereof.

When maleic acid or maleic anhydride are employed as the catalyst, the reaction mechanism is believed to go through an active oxidizing intermediate comprised of either peracetic acid or a synergistic combination of peracetic acid and permaleic acid. When phthalic acid is employed as the catalyst, the active oxidizing intemediate is believed to be either peracetic acid or a synergistic combination of peracetic acid and perphthalic acid. In either case, the use of in-situ generated peracetic acid is different from pre-formed peracetic acid in that the former is formed instantly and used instantly. However, the present invention is not limited to any particular reaction mechanism, but only to those reaction parameters stated to be critical.

The amount of catalyst is also critical to this invention. As can be seen by the Examples and Comparisons shown below. This oxidation reaction significantly decreases with the absence of these catalysts. It has been found that the amount of catalyst beneficial for running this oxidation reaction at a suitable rate is from about 0.1 to about 0.8, preferably from about 0.15 to about 0.5, moles of total catalyst per mole.

The mole ratio of $H_2O_2$ to 2-halopyridine should be from about 0.5:1 to about 5:1; preferably from about 1.2:1 to about 2.0:1. The mole ratio of acetic acid to 2-halopyridine should be from about 0.5:1 to about 2:1; preferably from about 0.75:1 to about 1.4:1. The employment of amounts of $H_2O_2$ and acetic acid below these mole ratios may cause a drop in product yields and above these mole ratios will decrease batch efficiency.

The reaction temperature should be from about 20° C. to about 120° C.; preferably, from about 60° C. to about 85° C. Temperatures below about 20° C. may result in too slow a reaction to be commercially feasible and temperatures above about 120° C. may cause uncontrollable reaction rate and side reactions. The reaction should be given sufficient time (e.g., from about 1 hour to 8 hours) to go to completion. After the reaction appears complete or at any desired time, the 2-halopyridine may be recovered from the reaction mixture by suitable means.

It is preferable to operate at atmospheric pressure but lower or higher pressures may be used if desired, for example, 0.75 to 5 atmospheres.

Depending upon the specific method by which the reactants are added to the reaction mixture, the time for completion of the reaction will vary with the reaction temperature and/or the speed at which the reactants are combined. The reaction time will decrease when the addition is speeded up or with an increase in temperature.

The in-situ generation of peracetic acid may be carried out in different ways. One preferred method is to simply combine $H_2O_2$, acetic acid, and the 2-halopyridine with the catalyst at room temperature (e.g., about 25° C.) and then raise the temperature of the reaction mixture to the desired temperature. Another preferred method is to combine acetic acid and the 2-halopyridine with the catalyst at room temperature, raise the temperature of this mixture to the desired temperature, and then add the $H_2O_2$ in incremental amounts.

Any suitable method for recovering the 2-halopyridine-N-oxide product from the reaction mixture may be employed. One preferred method is to neutralize the reaction mixture with a base (e.g., NaOH) followed by steam distillation under vacuum to remove the unreacted 2-halopyridine.

2-Chloropyridine-N-oxide or 2-bromopyridine-N-oxide made according to the process of this invention may be converted into sodium pyridine-2-thiol-N-oxide by a mercaptization step in which NaSH or $Na_2S$ in the presence of NaOH are reacted with the N-oxide compound. This conversion is described in U.S. Pat. No. 3,159,640, which issued to McClure and Shermer on Dec. 1, 1964.

Zinc pyridine-2-thiol-N-oxide may be made from the sodium pyridine-2-thiol-N-oxide by reacting the latter with a zinc salt (e.g., $ZnSO_4$ or $ZnCl_2$) See U.S. Pat. No. 4,080,329 which issued to Muntwyler on Mar. 21, 1979.

Besides 2-chloropyridine-N-oxide and 2-bromopyridine-N-oxide, the process of the present invention also contemplates the making of other halopyridine-N-oxides, including 2-fluoropyridine-N-oxide; 2-iodopyridine-N-oixde; corresponding 3- and 4-halopyridine-N-oxides 2,3-, 2,4-, 2,5-, 2,6-, and 3,5-dihalopyridine-N-oxides; and alkyl-substituted halopyridine-N-oxides such as 2-chloro-3-picoline-N-oxide, 2-chloro-4-picoline-N-oxide, 6-chloro-3-picoline-N-oxide, 6-chloro-2-picoline-N-oxide, and 6-chloro-2,4-lutidine-N-oxide.

The following Examples and Comparison are given to further illustrate the present invention. All parts and percentages are by weight unless explicity stated otherwise.

Use of Maleic Anhydride as Catalyst

The following ten (10) examples use maleic anhydride as a catalyst in amounts equal to 0.15 mole, 0.23 mole and 0.30 moles, respectively, per mole of 2-chloropyridine (2-PCl) reactant. These examples illustrate the beneficial effects resulting from using certain amounts of this catalyst.

EXAMPLES 1-10

Ten individual solutions containing 2-chloropyridine, acetic acid and maleic anhydride were prepared in a glass flask. Then a 50% aqueous hydrogen peroxide solution was added to each flask while keeping reaction temperature below 50° C. with a water bath.

The flasks were then held at 50° C. for 30 minutes before heating to 80° C. This preliminary hold time at 50° C. was to prevent thermal decomposition of $H_2O_2$ in the initial stages of the reaction.

When the level of remaining $H_2O_2$ in the reaction mixture fell below 1% by weight of the reaction mixture (this was determined by a standard titration method), the reaction mixture was cooled below 50° C. and NaOH was added to adjust the pH of the reaction mixture to 8.2. The pH adjustment makes the unreacted 2-chloropyridine come out of solution. Then the unreacted 2-chloropyridine is steam distilled under vacuum from the reaction mixture.

The remaining aqueous solution of 2-chloropyridine-N-oxide is assayed by a standard titanium trichloride titration method.

The molar ratios of maleic anhydride (MA) to 2-chloropyridine (2-PCl), $H_2O_2$ to 2-chloropyridine and acetic acid ($CH_3CO_2H$) to 2-chloropyridine for each of these ten examples are given in Table I, below. Also given in Table I are % 2-chloropyridine conversion along with the uncorrected yield and selectivity of 2-chloropyridine-N-oxide product.

Use of No Catalyst

The following Comparision uses no maleic anhydride, maleic acid or phthalic anhydride catalyst. This illustrates the adverse effects of using no catalyst.

Comparison I

A solution containing 2-chloropyridine and acetic acid was prepared in a glass flask. Then a 50% by weight aqueous $H_2O_2$ solution was added to the flask while keeping the reaction temperature below 50° C. with a water bath. The same procedure as used in Examples 1-10 was followed to obtain a 2-chloropyridine-N-oxide product except the reaction temperature was 70° C. instead of 80° C.

The mole ratios, reaction time and the assay results are also given in Table I.

As can be seen, the uncorrected yield, selectivity, and conversion are all far below the Examples which use the catalyst.

TABLE I

| | | | Use of Maleic Anhydride (MA) As Catalyst | | | | |
|---|---|---|---|---|---|---|---|
| Comparison or Example | MA:2-PCl Mole Ratio | $H_2O_2$:2-PCl Mole Ratio | $CH_3CO_2H$:2-PCl Mole Ratio | Reaction Time (hrs.) | % 2-PCl Conversion | 2-PCl—N—Oxide Uncorr. Yield | Selectivity |
| C-1 | 0:1 | 1:1 | 1.2:1 | 3.0 | 11.8 | 8.1 | 68.6 |
| 1 | 0.15:1 | 1.5:1 | 1.34:1 | 4.0 | 55.2 | 52.1 | 94.4 |
| 2 | 0.15:1 | 1.75:1 | 1.34:1 | 5.0 | 62.0 | 56.6 | 91.3 |
| 3 | 0.30:1 | 1.5:1 | 1.34:1 | 2.5 | 61.4 | 60.4 | 98.3 |
| 4 | 0.30:1 | 1.75:1 | 1.34:1 | 2.8 | 66.8 | 64.1 | 95.7 |
| 5 | 0.15:1 | 1.5:1 | 1:1 | 5.5 | 49.9 | 50.3 | 100.8 |
| 6 | 0.15:1 | 1.75:1 | 1:1 | 6.0 | 59.8 | 55.8 | 93.4 |
| 7 | 0.23:1 | 1.75:1 | 1:1 | 4.5 | 62.7 | 60.0 | 95.7 |
| 8 | 0.30:1 | 1.75:1 | 1:1 | 3.0 | 66.8 | 64.1 | 95.9 |
| 9 | 0.30:1 | 1.75:1 | 1:1 | 3.0 | 69.3 | 67.2 | 96.9 |
| 10 | 0.30:1 | 1.75:1 | 0.84:1 | 2.8 | 65.1 | 62.6 | 96.1 |

USE OF MALEIC ACID AS CATALYST

EXAMPLE 11

The procedure employed in Examples 1-10 was repeated except that maleic acid (ME) was used as a catalyst instead of maleic anhydride. The process parameters and product assays are given in Table II.

As can be seen from the results shown in Table II, the % 2-chloropyridine conversion and 2-chloropyridine-N-oxide yield and selectivity are generally lower than the results obtained with maleic anhydride catalyst.

TABLE II

| | | Use of Maleic Acid (ME) As Catalyst | | | | | |
|---|---|---|---|---|---|---|---|
| Example | ME:2-PSl Mole Ratio | $H_2O_2$:2-PCl Mole Ratio | $CH_3CO_2H$:2-PCl Mole Ratio | Reaction Time (hrs.) | % 2-PCl Conversion | 2-PCl—N—Oxide Uncorr. Yield | Selectivity |
| 11 | 0.3:1 | 1.75:1 | 1:1 | 3.8 | 58.1 | 54.4 | 93.6 |

USE OF PHTHALIC ACID AS CATALYST

EXAMPLE 12

The procedure employed in Examples 1-10 was repeated except the phthalic anhydride was used as a catalyst instead of maleic anhydride. The process parameters and product assays are given in Table III.

As can be seen from the results shown in Table II, the % 2-chloropyridine conversion and 2-chloropyridine-N-oxide yield and selectivity are generally lower than the results obtained with maleic anhydride catalyst.

TABLE III

| | | Use of Phthalic Acid (PA) As Catalyst | | | | | |
|---|---|---|---|---|---|---|---|
| Example | PA:2-PCl Mole Ratio | $H_2O_2$:2-PCl Mole Ratio | $CH_3CO_2H$:2-PCl Mole Ratio | Reaction Time (hrs.) | % 2-PCl Conversion | 2-PCl—N—Oxide Uncorr. Yield | Selectivity |
| 12 | 0.3:1 | 1.75:1 | 1:1 | 5.8 | 57.2 | 51.4 | 89.9 |

PREPARATION OF SODIUM AND ZINC PYRIDINE-2-THIOL-N-OXIDE

The following Examples 13–23 illustrate that sodium and pyridine-2-thiol-N-oxide may be made from the 2-chloropyridine-N-oxide products made by Examples 1–4 and 6–12.

EXAMPLES 13–23

A. Preparation of Sodium Pyridine-2-thiol-N-oxide

To an aqueous solution of 2-chloropyridine-N-oxide (0.20 mole) was added an aqueous sodium hydrosulfide solution (0.29 moles, 24.6% by weight) and the reaction mixture was heated at 75° C. To this was added 20% aqueous sodium hydroxide solution as needed to maintain the pH at 9.5 (run time about 1.75 hours). The pH was then adjusted to 6.2 with hydrochloric acid while puring with nitrogen at 75° C. over 0.5 hours. The mixture was then cooled to 25° C. and filtered.

B. Preparation of Zinc Pyridine-2-thiol-N-oxide

The pH of the filtrate from A (contains about 0.20 mole sodium pyridine-2-thiol-N-oxide) was adjusted to 6.5 and a 20% zinc sulfate solution added until no free sodium 2-thiol-N-oxide was detected (via a ferric chloride test). The mixture was stirred 0.5 hours, filtered and washed with water. The "wet cake" was used for color determination using a Hunter Lab Color/Difference Meter D 25DZ, according to AATCC test method 110-1972. A portion was dried and analyzed via titration.

Comparing the color analysis of these examples as shown in Table IV to the color analysis of an alternative process given in Examples 12 and 13 of U.S. patent application Ser. No. 362,707, one can see that the material of this invention is considerably whiter (1.8–3.9 values for "b" vs. 5.2 and 4.9 for "D" in the U.S. patent application Examples 12 and 13.)

Comparing the purity of the derived Zinc pyridine-2-thiol-N-oxide one can see that the material of this invention is purer (97.7–99.1% assay vs. 96.1–97.1% assay for examples 12 and 13 in the forementioned U.S. patent application).

TABLE IV

| Synthesis Example | Example | ZnPT Yield (Based on 2-PCl) | ZnPT Assay | Color Analysis L | a | b |
|---|---|---|---|---|---|---|
| 1 | 13 | 86.4% | 97.7% | 94.7 | −4.7 | 2.9 |
| 2 | 14 | 85.8% | 98.8% | 94.8 | −4.7 | 3.4 |
| 3 | 15 | 90.7% | 98.0% | 95.1 | −4.8 | 2.5 |
| 4 | 16 | 89.3% | 98.9% | 94.9 | −4.7 | 1.8 |
| 6 | 17 | 84.8% | 99.0% | 93.7 | −4.7 | 3.5 |
| 7 | 18 | 85.6% | 98.6% | 93.9 | −4.8 | 2.6 |
| 8 | 19 | 92.8% | 99.0% | 94.4 | −4.6 | 2.6 |
| 9 | 20 | 87.1% | 98.4% | 94.1 | −5.1 | 3.0 |
| 10 | 21 | 91.4% | 99.1% | 93.9 | −4.9 | 2.8 |
| 11 | 22 | 85.9% | 97.9% | 93.7 | −4.4 | 2.2 |
| 12 | 23 | 82.5% | 98.3% | 91.4 | −3.3 | 3.9 |

What is claimed is:

1. A method of producing a 2-halopyridine-N-oxide comprising
    reacting at a temperature from about 20° C. to about 120° C. (a) hydrogen peroxide, (b) a 2-halopyridine selected from the group consisting of 2-chloropyridine and 2-bromopyridine, and (c) acetic acid in the presence of a catalyst selected from the group consisting of maleic acid, maleic anhydride, phthalic anhydride, and mixtures thereof, in order to produce the corresponding 2-halopyridine-N-oxide; said reaction carried out by employing from about 0.5 to about 5.0 moles of $H_2O_2$ per mole of 2-halopyridine; employing from about 0.5 to about 2.0 moles of acetic acid per mole of 2-halopyridine, and employing from about 0.1 to about 0.8 moles of catalyst per mole of 2-halopyridine.

2. The method of claim 1 wherein said halopyridine is 2-chloropyridine.

3. The method of claim 1 wherein said catalyst is maleic anhydride.

4. The method of claim 1 wherein about 1.2 to about 2.0 moles of $H_2O_2$ are employed per mole of 2-halopyridine.

5. The method of claim 1 wherein said $H_2O_2$ is employed in the form of an aqueous solution containing about 30% to about 90% by weight $H_2O_2$.

6. The process of claim 1 wherein about 0.75 to about 1.4 moles of acetic acid are employed per mole of 2-halopyridine.

7. The process of claim 1 wherein about 0.15 to about 0.5 moles of catalyst are employed per mole of 2-halopyridine.

8. The process of claim 1 wherein said reacting step is carried out at a temperature from about 60° C. to about 85° C.

9. A method for producing a 2-halopyridine-N-oxide comprising
    reacting at a temperature from about 20° C. to about 120° C. (a) an aqueous solution containing from about 40% to about 70% by weight $H_2O_2$, (b) a 2-halopyridine selected from the group consisting of 2-chloropyridine and 2-bromopyridine, and (c) acetic acid in the presence of maleic anhydride in order to produce the corresponding 2-halopyridine-N-oxide; said reaction carried out by employing from about 1.2 to about 2.0 moles of $H_2O_2$ per mole of 2-halopyridine; employing from about 0.75 to about 1.4 moles of acetic acid per mole of 2-halopyridine, and employing from about 0.15 to about 0.5 moles of maleic acid per mole of 2-halopyridine.

10. The method of claim 9 wherein said 2-halopyridine is 2-chloropyridine.

11. The method of claim 9 wherein said reaction temperature is from about 60° C. to about 85° C.

* * * * *